United States Patent
Gregersen et al.

(10) Patent No.: US 10,492,912 B2
(45) Date of Patent: Dec. 3, 2019

(54) INTERBODY SPINAL FUSION IMPLANT HAVING LOCKING ELEMENTS WITH LATERAL DISPLACEMENT

(71) Applicant: Innovasis, Inc., Salt Lake City, UT (US)

(72) Inventors: Colin S. Gregersen, Salt Lake City, UT (US); Brandon Walker, Layton, UT (US)

(73) Assignee: Innovasis, Inc., Salt Lake City, UT (US)

( * ) Notice: Subject to any disclaimer, the term of this patent is extended or adjusted under 35 U.S.C. 154(b) by 210 days.

(21) Appl. No.: 15/680,330

(22) Filed: Aug. 18, 2017

(65) Prior Publication Data

US 2019/0053907 A1 Feb. 21, 2019

(51) Int. Cl.
  *A61F 2/44* (2006.01)
  *A61F 2/30* (2006.01)
  *A61B 17/80* (2006.01)

(52) U.S. Cl.
  CPC ...... *A61F 2/30749* (2013.01); *A61B 17/8042* (2013.01); *A61F 2/442* (2013.01); *A61F 2/447* (2013.01); *A61F 2/4455* (2013.01); *A61F 2/30767* (2013.01); *A61F 2002/30004* (2013.01); *A61F 2002/30331* (2013.01); *A61F 2002/30507* (2013.01); *A61F 2002/30787* (2013.01); *A61F 2002/4475* (2013.01)

(58) Field of Classification Search
  CPC .................................................... A61F 2/4455
  See application file for complete search history.

(56) References Cited

U.S. PATENT DOCUMENTS

| | | |
|---|---|---|
| 6,432,106 B1 | 8/2002 | Fraser |
| 6,485,517 B1 | 11/2002 | Michaelson |
| 6,558,423 B1 | 5/2003 | Michaelson |
| 6,682,530 B2 | 1/2004 | Dixon et al. |
| 6,835,206 B2 | 12/2004 | Jackson |
| 6,849,093 B2 | 2/2005 | Michelson |
| 7,004,944 B2 * | 2/2006 | Gause ............... A61B 17/8042 606/294 |
| 7,033,394 B2 | 4/2006 | Michaelson |
| 7,077,864 B2 | 7/2006 | Byrd, III et al. |
| 7,846,207 B2 | 12/2010 | Lechmann et al. |

(Continued)

FOREIGN PATENT DOCUMENTS

| | | |
|---|---|---|
| EP | 2 510 904 A1 | 10/2012 |
| WO | 2000/066044 A1 | 11/2000 |
| WO | 2000/066045 A1 | 11/2000 |

*Primary Examiner* — Nicholas W Woodall
(74) *Attorney, Agent, or Firm* — Workman Nydegger

(57) ABSTRACT

An interbody spinal fusion implant includes a tapered body and a faceplate secured to the tapered body. The faceplate has a recess formed on a front face of the faceplate that is at least partially bounded by an interior surface. A first screw hole and a spaced apart first locking slot pass through the faceplate, the first locking slot having an elongated width. A first locking screw has a head and a threaded shaft, the threaded shaft passing through the first locking slot and being sized so that the threaded shaft can slide laterally along a length of the elongated width of the first locking slot. A first nut is disposed between the tapered body and the faceplate, the shaft of the first locking screw being threadedly engaged with the first nut.

23 Claims, 12 Drawing Sheets

(56) References Cited

U.S. PATENT DOCUMENTS

| | | |
|---|---|---|
| 7,862,616 B2 | 1/2011 | Lechmann et al. |
| 7,875,076 B2 | 1/2011 | Mathieu et al. |
| 8,182,539 B2 | 5/2012 | Tyber et al. |
| 8,277,493 B2 | 10/2012 | Farris et al. |
| 8,282,675 B2 | 10/2012 | Maguire et al. |
| 8,328,872 B2 | 12/2012 | Duffield et al. |
| 8,403,986 B2 | 3/2013 | Michelson |
| 8,454,700 B2 | 6/2013 | Lemoine et al. |
| 8,709,085 B2 | 4/2014 | Lechmann et al. |
| 8,715,354 B2 | 5/2014 | Lechmann et al. |
| 8,764,831 B2 | 7/2014 | Lechmann et al. |
| 8,814,912 B2 | 8/2014 | Carlson et al. |
| 8,828,084 B2 | 9/2014 | Aflatoon et al. |
| 8,882,813 B2 | 11/2014 | Jones et al. |
| 8,882,814 B2 | 11/2014 | Suh |
| 9,005,295 B2 | 4/2015 | Kueenzi et al. |
| 9,980,824 B2 * | 5/2018 | Zappacosta ............ A61F 2/4455 |
| 10,265,109 B2 * | 4/2019 | Lauf .................. A61B 17/7059 |
| 2009/0210062 A1 | 8/2009 | Thalgott et al. |
| 2011/0251689 A1 | 10/2011 | Seifert et al. |
| 2013/0268008 A1 | 10/2013 | McDonough et al. |
| 2013/0282017 A1 | 10/2013 | Moskowitz et al. |
| 2014/0039623 A1 * | 2/2014 | Iott ..................... A61F 2/30744 |
| | | 623/17.16 |
| 2014/0243985 A1 | 8/2014 | Lechmann et al. |
| 2014/0277495 A1 | 9/2014 | Muhanna |
| 2015/0025635 A1 | 1/2015 | Laubert |
| 2015/0051704 A1 | 2/2015 | Duffield et al. |
| 2015/0328005 A1 * | 11/2015 | Padovani ................ A61F 2/442 |
| | | 623/17.13 |

* cited by examiner

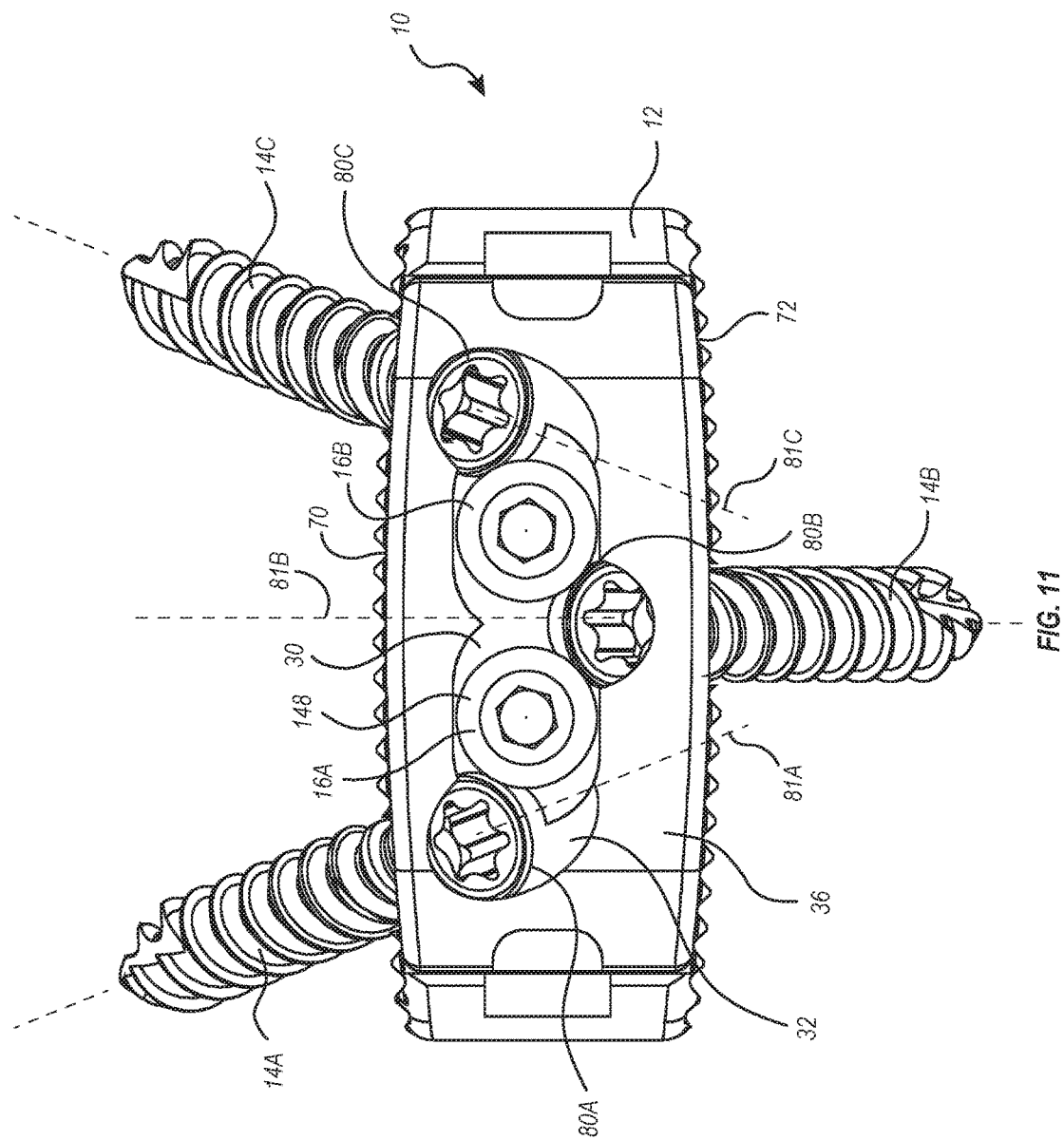

INTERBODY SPINAL FUSION IMPLANT HAVING LOCKING ELEMENTS WITH LATERAL DISPLACEMENT

CROSS-REFERENCE TO RELATED APPLICATIONS

Not applicable.

BACKGROUND OF THE INVENTION

1. The Field of the Invention

The present invention relates to interbody spinal fusion implants and, more specifically, to interbody spinal fusion implants having laterally displaceable locking elements for selectively locking bone screws.

2. The Relevant Technology

The spinal column is made up of spaced apart vertebra that are each separated by a cushioning disc. If a disc ruptures or is otherwise damaged, the adjacent vertebra can press against the spinal cord which can cause pain and loss of mobility. In one approach to treating a damaged disc, at least a portion of the damaged disc is removed and a spinal fusion implant is inserted between the adjacent vertebra. The implant keeps the vertebra separated to prevent the vertebra from pressing on the spinal cord. Eventually, the adjacent vertebra fuse together about the implant so as to preclude any movement between the vertebra.

To help fuse the vertebra together, the implant is formed with a hollow cavity that is manually filled with a bone growth material, such as bone allograft, prior to insertion between the vertebra. The openings on the implant enable the bone allograft to facilitate bone growth between the vertebra.

To help keep the implant properly positioned and stationary as the adjacent vertebra are fusing together, bone screws are passed through the implant and are screwed into the adjacent vertebra. One risk associated with using bone screws is that through movement of the patient, the bone screws can work loose and back out of the implant. The movement of the bone screws can cause the implant to become loose and prevent proper fusing between the vertebra. In addition, the loose bone screw becomes a risk to the patient as it can create obstructions or damage surrounding bone or tissue.

Various approaches have been used to help lock bone screws to spinal implants. Such approaches, however, have typically suffered from shortcomings such as being ineffective, difficult to use, or having a relatively high risk that all or a portion of the implant will dislodge within the patient. Accordingly, what is needed in the art are spinal implants having improved assemblies and methods for locking bone screws to the implant.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

FIG. 11 is a front elevational view of the fusion implant shown in FIG. 1 with the locking screws in an advanced first position.

DETAILED DESCRIPTION OF THE PREFERRED EMBODIMENTS

Figure 1:
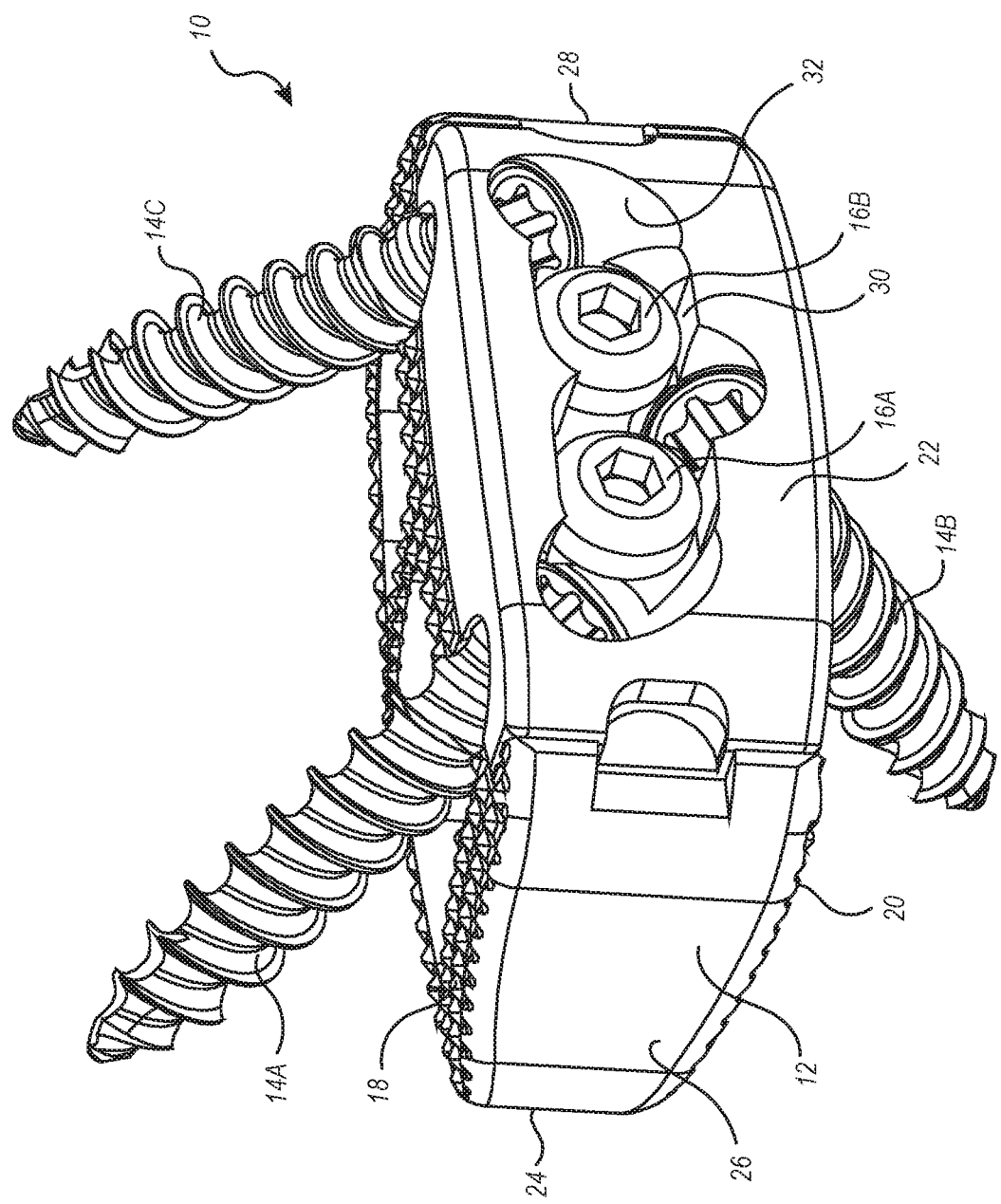
FIG. 1 is a perspective view of an interbody spinal fusion implant incorporating features of the present invention.

Before describing various embodiments of the present disclosure in detail, it is to be understood that this disclosure is not limited to the parameters of the particularly exemplified implants, methods, systems and/or products, which may, of course, vary. Thus, while certain embodiments of the present disclosure will be described in detail, with reference to specific configurations, parameters, features (e.g., components, members, elements, parts, and/or portions), etc., the descriptions are illustrative and are not to be construed as limiting the scope of the claimed invention. In addition, the terminology used herein is for the purpose of describing the embodiments, and is not necessarily intended to limit the scope of the claimed invention.

Unless defined otherwise, all technical and scientific terms used herein have the same meaning as commonly understood by one of ordinary skill in the art to which the present disclosure pertains.

Various aspects of the present disclosure, including implants, systems, processes, and/or products may be illustrated with reference to one or more embodiments or implementations, which are exemplary in nature. As used herein, the terms "embodiment" and "implementation" mean "serving as an example, instance, or illustration," and should not necessarily be construed as preferred or advantageous over other aspects disclosed herein. In addition, reference to an "implementation" of the present disclosure or invention includes a specific reference to one or more embodiments thereof, and vice versa, and is intended to provide illustrative examples without limiting the scope of the invention, which is indicated by the appended claims rather than by the following description.

As used throughout this application the words "can" and "may" are used in a permissive sense (i.e., meaning having the potential to), rather than the mandatory sense (i.e., meaning must). Additionally, the terms "including," "having," "involving," "containing," "characterized by," as well as variants thereof (e.g., "includes," "has," and "involves,"

"contains," etc.), and similar terms as used herein, including the claims, shall be inclusive and/or open-ended, shall have the same meaning as the word "comprising" and variants thereof (e.g., "comprise" and "comprises"), and do not exclude additional, un-recited elements or method steps, illustratively.

It will be noted that, as used in this specification and the appended claims, the singular forms "a," "an" and "the" include plural referents unless the context clearly dictates otherwise. Thus, for example, reference to a "locking screw" includes one, two, or more locking screws.

As used herein, directional terms, such as "top," "bottom," "left," "right," "up," "down," "upper," "lower," "proximal," "distal," "vertical," "horizontal" and the like are used herein solely to indicate relative directions and are not otherwise intended to limit the scope of the disclosure and/or claimed invention.

Various aspects of the present disclosure can be illustrated by describing components that are bound, coupled, attached, connected, and/or joined together. As used herein, the terms "bound," "coupled", "attached", "connected," and/or "joined" are used to indicate either a direct association between two components or, where appropriate, an indirect association with one another through intervening or intermediate components. In contrast, when a component is referred to as being "directly bound," "directly coupled", "directly attached", "directly connected," and/or "directly joined" to another component, no intervening elements are present or contemplated. Furthermore, binding, coupling, attaching, connecting, and/or joining can comprise mechanical and/or chemical association.

To facilitate understanding, like reference numerals (i.e., like numbering of components and/or elements) have been used, where possible, to designate like elements common to the figures. Specifically, in the exemplary embodiments illustrated in the figures, like structures, or structures with like functions, will be provided with similar reference designations, where possible.

Specific language will be used herein to describe the exemplary embodiments. Nevertheless, it will be understood that no limitation of the scope of the disclosure is thereby intended. Rather, it is to be understood that the language used to describe the exemplary embodiments is illustrative only and is not to be construed as limiting the scope of the disclosure (unless such language is expressly described herein as essential). Furthermore, multiple instances of an element and or sub-elements of a parent element may each include separate letters appended to the element number. An element label with an appended letter can be used to designate an alternative design, structure, function, implementation, and/or embodiment of an element or feature without an appended letter. Likewise, an element label with an appended letter can be used to indicate a sub-element of a parent element. However, element labels including an appended letter are not meant to be limited to the specific and/or particular embodiment(s) in which they are illustrated. In other words, reference to a specific feature in relation to one embodiment should not be construed as being limited to applications only within said embodiment.

Furthermore, multiple instances of the same element may each include separate letters appended to the element number. For example, two instances of a particular element "20" may be labeled as "20a" and "20b". In that case, the element label may be used without an appended letter (e.g., "20") to generally refer to every instance of the element; while the element label will include an appended letter (e.g., "20a") to refer to a specific instance of the element.

It will also be appreciated that where multiple possibilities of values or a range a values (e.g., less than, greater than, at least, or up to a certain value, or between two recited values) is disclosed or recited, any specific value or range of values falling within the disclosed range of values is likewise disclosed and contemplated herein.

Depicted in FIG. 1 is one embodiment of an inventive interbody spinal fusion implant 10 incorporating features of the present invention and intended for use in fusing together adjacent vertebra of a spine. In general, fusion implant 10 comprises a fusion spacer 12 having bone screws 14A, 14B, and 14C removably disposed thereon. A pair of locking screws 16A and 16B are adjustably mounted on fusion pacer 12 and are used to prevent unwanted movement or removal of bone screws 14A-C from fusion spacer 12 once fusion spacer 10 has been implanted in the spine. The various elements of fusion implant 10 will now be described in greater detail.

When viewed as a whole, fusion spacer 12 has a top surface 18 and an opposing bottom surface 20 that extend between a front face 22 and an opposing back face 24 and that also extend between opposing side faces 26 and 28. For reference purposes, fusion spacer 12 has a vertical direction extending between top surface 18 and opposing bottom surface 20 and a horizontal or lateral direction extending between opposing side faces 26 and 28. Fusion spacer 12 is wedge-shaped and inwardly tapers from front face 22 to back face 24. Top surface 18 and bottom surface 20 can be linear but typically have a slight convex arch or curve extending from front face 22 to back face 24. Fusion spacer 12 can also be bi-convex with top surface 18 and bottom surface 20 also having slight convex arch or curve extending between opposing side faces 26 and 28. Formed on front face 22 is an elongated recess 30 that is at least partially bounded by an interior surface 32. Locking screws 16A and 16B are at least partially disposed within recess 30.

Figure 2:
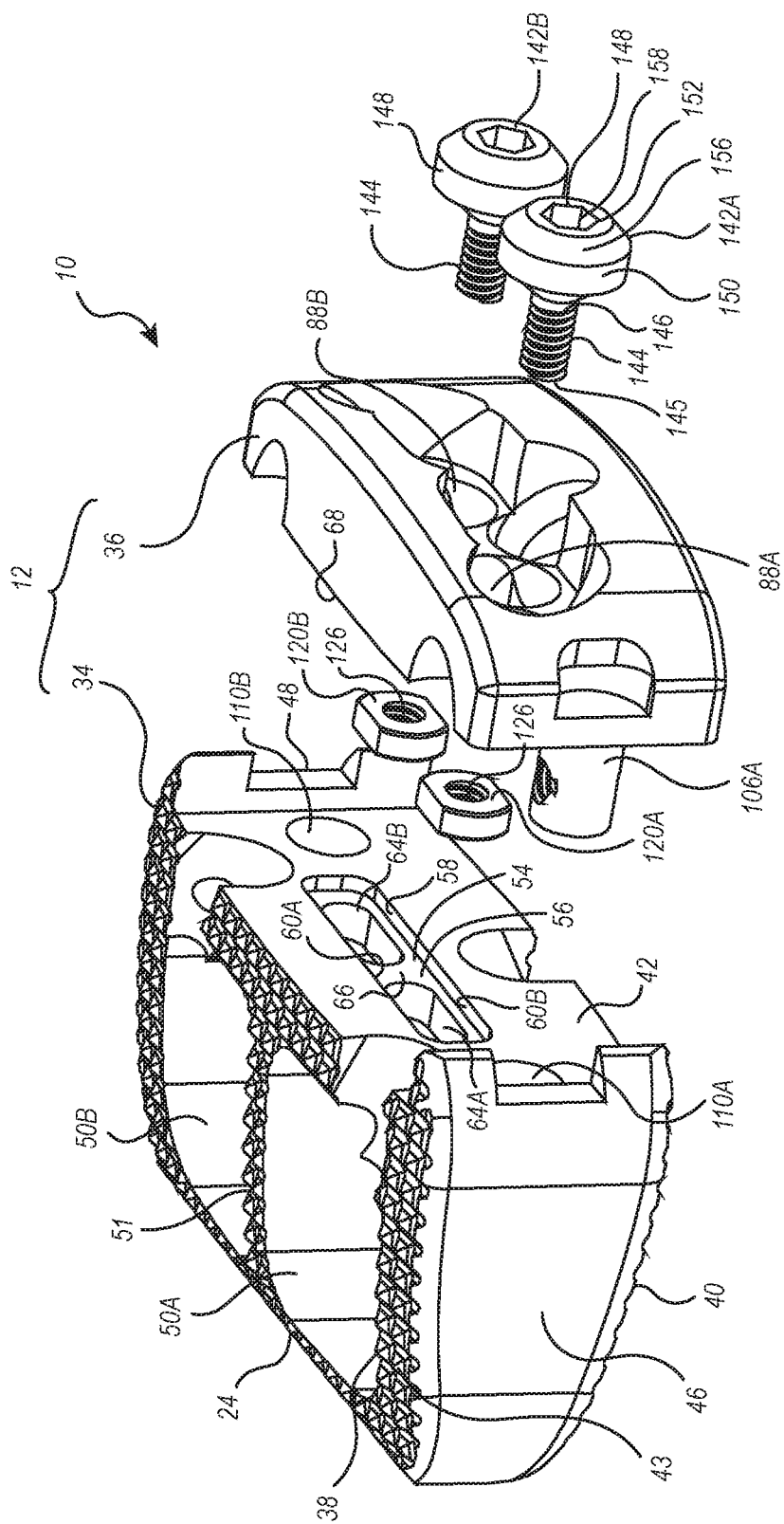
FIG. 2 is an exploded view of a portion of the fusion implant shown in FIG. 1.

Turning to FIG. 2, fusion spacer 12 is further defined as comprising a body 34 and a faceplate 36 that are selectively coupled together. Body 34 comprises a top surface 38 and an opposing bottom surface 40 that extend between a front face 42 and opposing back face 24 and that also extend between a first side face 46 and an opposing second side face 48. Again, body 34 is wedge shaped and inwardly tapers from front face 42 to back face 24. Top surface 38 and bottom surface 40 can be linear but typically have a slight convex arch or curve extending from front face 42 to back face 24 and can also have a slight convex arch or curve extending opposing side faces 46 and 48. A plurality of teeth 43 can be formed on top surface 38 and bottom surface 40. Extending through body 34 between top face 38 and bottom face 40 are a pair of cavities 50A and 50B separated by a bridge 51. Cavities 50 are configured to receive a bone growth material, which can be autologous, allograft or synthetic, for use in fusing together adjacent vertebrae. It is appreciated that cavities 50 can be different sizes, shapes, and numbers. For example, 1, 3, 4, or other numbers of cavities can be formed extending through body 34.

Centrally recessed on front face 42 of body 34 is an elongated channel 54. Channel 54 is partially bounded by a floor 56 and an encircling sidewall 58. Channel 54 has a rectangular configuration with rounded corners and has a longitudinal axis that extends laterally between side faces 46 and 48 of body 34. Encircling sidewall 58 includes a top wall portion 60A and an opposing bottom wall portion 60B that are linear and are disposed in parallel alignment. Wall portions 60A and 60B also extend laterally and can be disposed in parallel alignment with the longitudinal axis of channel 54.

Recessed within floor 56 of channel 54 is a first access slot 64A and a spaced apart second access slot 64B. Access slots 64 have an elongated width and can each have the same configuration. Access slots 64 each have a longitudinal axis that extends laterally between side faces 46 and 48. The longitudinal axis of access slots 64 can also be parallel to and horizontally aligned with the longitudinal axis of channel 54.

Access slots 64 can be centrally formed on floor 56 (in a vertical direction) so as to be spaced apart encircling sidewall 58. In other embodiments, portions of access slots 64 can extend to sidewall 58. In the embodiment depicted, a brace 66 is centrally disposed between access slots 64A and 64B. In an alternative embodiment, however, brace 66 can be removed so that a single access slot 64 is formed on floor 56 that extends the length of access slots 64A and 64B.

Body 34 is typically molded, milled or otherwise formed from a biocompatible material such as a polyetheretherketone (PEEK) polymer that can be reinforced with a fiber, such as carbon fiber, and/or other additives. In alternative embodiments, body 34 can be formed from medical grade biocompatible metals (such as titanium), alloys, polymers, ceramics, or other materials that have adequate strength.

Figure 3:
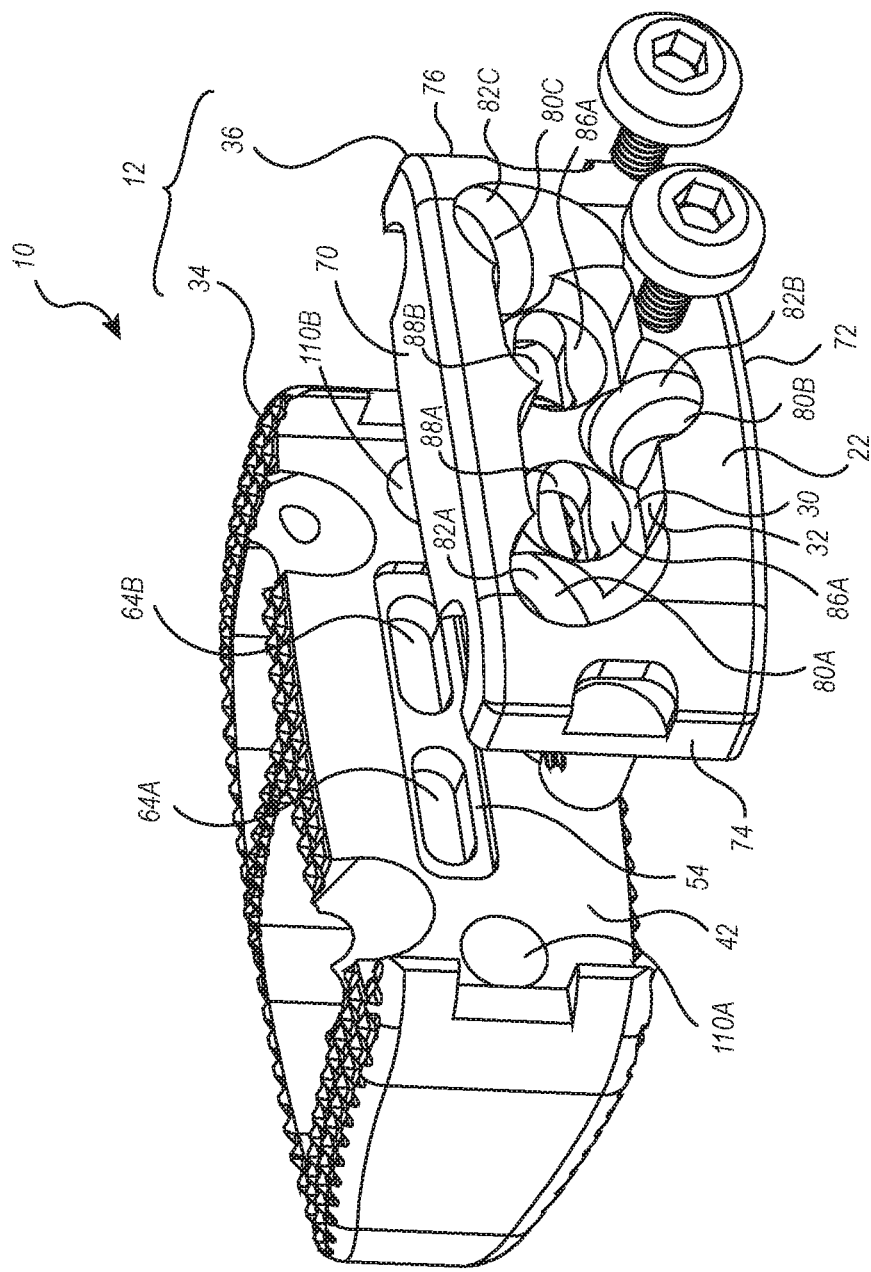
FIG. 3 is a front perspective view of the fusion spacer of the fusion implant shown in FIG. 1.
Figure 4:
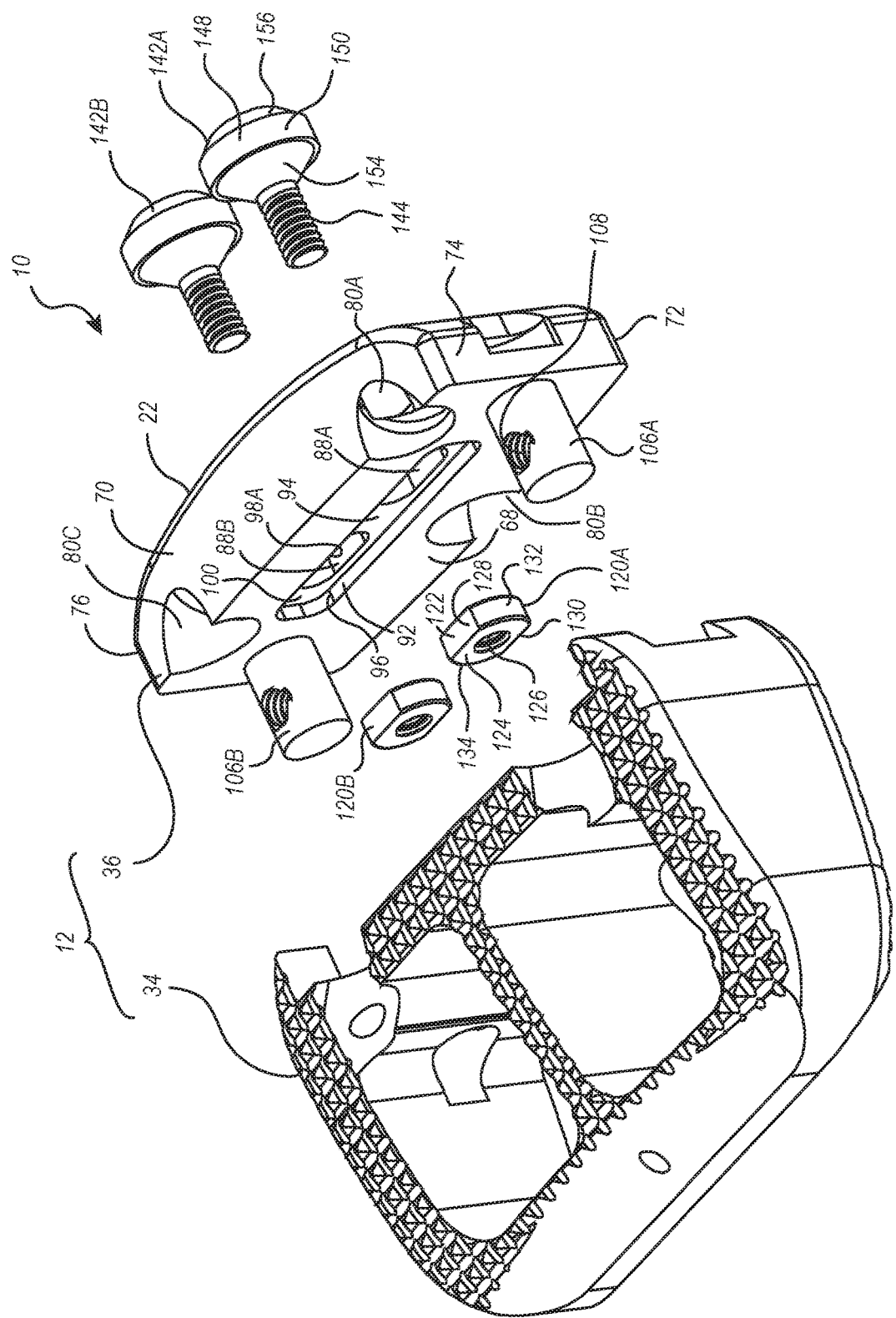
FIG. 4 is a rear perspective view of the fusion spacer shown in FIG. 3.

As depicted in FIGS. 3 and 4, faceplate 36 includes front face 22 and an opposing back face 68 that both extend between a top face 70 and an opposing bottom face 72 and that extend between opposing side faces 74 and 76. As previously discussed, elongated recess 30 is formed on front face 22 and is partially bounded by interior surface 32. Elongated recess 30 has a longitudinal axis that extends laterally between opposing side faces 74 and 76.

Extending through faceplate 36 from interior surface 32 to back face 68 are three screw holes 80A, 80B, and 80C. Screw holes 80A-C are configured to receive bone screws 14A-C, respectively. As depicted in FIG. 11, screw holes 80A and 80C are disposed at the opposing ends of recess 30 with each having a central longitudinal axis 81A and 81C, respectively, that is sloped. Specifically, axis 81A slopes forward and away from faceplate 36 at a vertical orientation that is downward toward bottom face 72 and a horizontal orientation that is inward toward the center of recess 30. Likewise, axis 81C also slopes forward and away from faceplate 36 at a vertical orientation that is downward toward bottom face 72 and a horizontal orientation that is inward toward the center of recess 30. In this orientation, screw holes 80A and 80C pass out through back face 68 of faceplate 36 so as to partially intersect with top face 70 as shown in FIG. 4.

Returning to FIG. 11, screw hole 80B is centrally located between screw holes 80A and 80C and slopes forward and away from faceplate 36 at a vertical orientation that is upward toward top face 70 and a horizontal orientation that is toward the center of recess 30. As such, screw hole 80B also passes out through back face 68 of faceplate 36 so as to partially intersect with bottom face 72 as shown in FIG. 4. As depicted in FIG. 3, each screw hole 80A-C has an annular, inwardly tapered, chamfer 82A-C, respectively, that is formed at the start of or within each screw hole 80A-C. Each annular chamfer 82 provides an annular seat against which the head of each corresponding bone screw 14A-C sits, as discussed below, so that bone screws 14 cannot pass through faceplate 36.

Continuing with FIG. 3, formed on interior surface 32 of recess 30 between first screw hole 80A and second screw hole 80B is a first centering recess 86A. Centering recess 86 is typically circular having an annular taper that inwardly extends to a central area. Centering recess 86 can be a conical recess, an annular concave recess, a hemispherical recess or have other tapered configurations. An elongated first locking slot 88A is centrally formed on centering recess 86 and extends through faceplate 36. Locking slot 88A is elongated having an elongated width and a longitudinal axis that extends laterally between side faces 74 and 76. A centering recess 86B is also formed on interior surface 32 between screw hole 80B and screw hole 80C. Centering recess 86B can have the same configuration as centering recess 86A discussed above. A second locking slot 88B is centrally formed on centering recess 86B and extends through faceplate 36. Second locking slot 88B can have the same configuration and orientation as first locking slot 88A, as discussed above. In addition, locking slots 88A and 88B can have the same size inner dimensions as access slots 64A and 64B, previously discussed.

As depicted in FIG. 4, a channel 92 is centrally formed on back face 68 of faceplate 36 and is bounded by a floor 94 and encircling sidewall 96. Channel 92 has a substantially rectangular configuration with a longitudinal axis that extends laterally between side faces 74 and 76. Likewise, sidewall 96 includes a top wall portion 98A and a bottom wall portion 98B that are linear and are disposed in parallel alignment.

Figure 6:
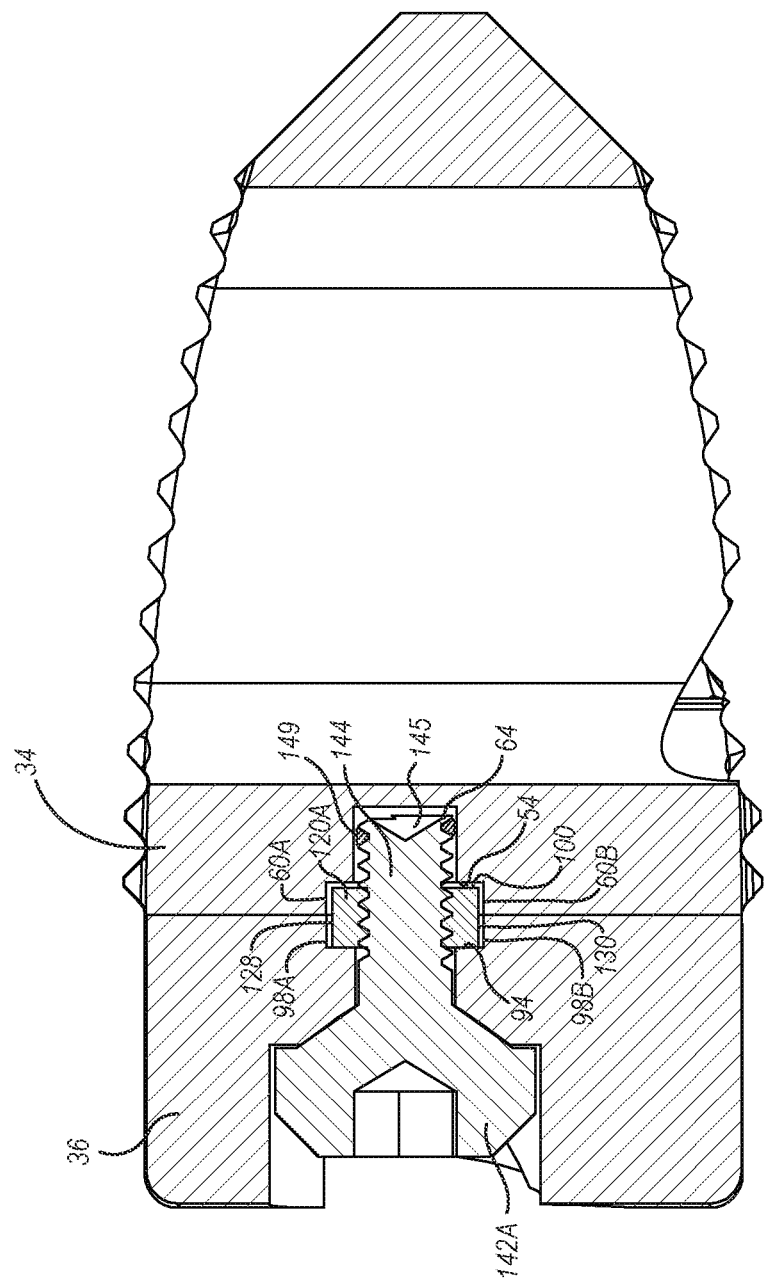
FIG. 6 is a cross sectional side view of the fusion implant shown in FIG. 1.

Channel 92 of faceplate 36 can have the same size and configuration as channel 54 of body 34 (FIG. 2) so that when faceplate 36 is coupled with body 34, as discussed below, channels 54 and 92 align and combine to form an elongated slide channel 100 (FIG. 6). Slide channel 100 is bounded between faceplate 36 and body 34 and, more specifically, is bounded between floors 54 and 94. In an alternative embodiment, it is appreciated that floor 54 on body 34 can be eliminated and that two enlarged access slots 64A and 64B or one elongated access slot 64 could extend all the way to cavities 50. As such, slide channel 100 may only be bounded on one side. In this embodiment, it is also envisioned that faceplate 36 and body 34 could be formed as a single, integral, continuous member forming fusion spacer 12 as opposed to two separate members that are connected together.

Locking slots 88A and 88B extend through floor 94 of faceplate 36 so as to communicate with channel 92. Locking slots 88A and 88B can extend through floor 94 in the same position and orientation that access slots 64 extend through floor 56 of body 34. Locking slots 88A and B can also have the same size and configuration as access slots 64A and B so that when faceplate 36 and body 34 are coupled together, locking slots 88A and B are aligned with access slots 64A and B, respectively.

Faceplate 36 is typically molded, milled or otherwise formed from a biocompatible material such as titanium or some other biocompatible metal. Other materials can also be used. Faceplate 36 and body 34 are typically made from different materials but can be made from the same material, such as titanium or other biocompatible metal.

Figure 5:
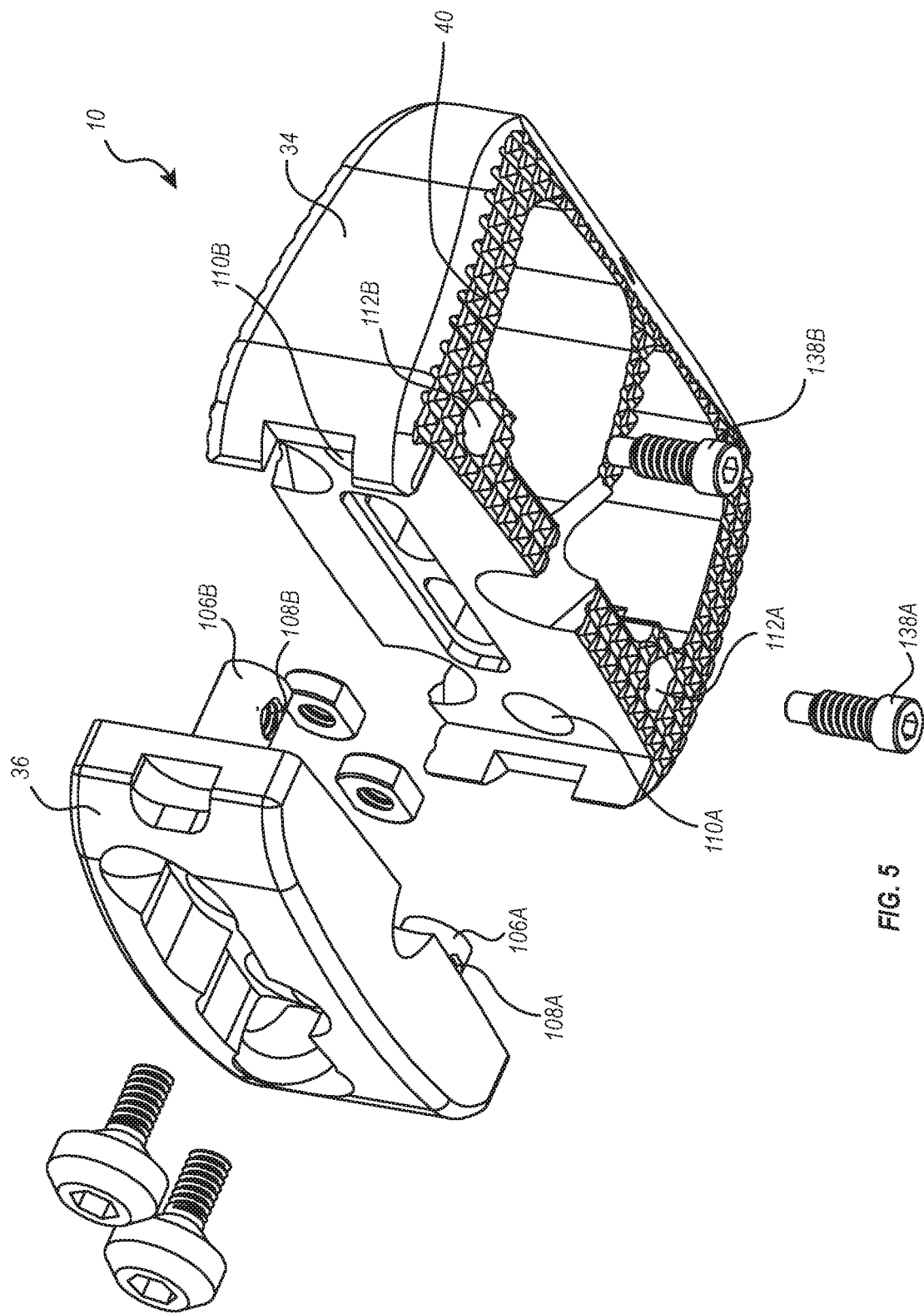
FIG. 5 is a bottom perspective view of the fusion spacer shown in FIG. 3.

To facilitate the coupling of faceplate 36 to body 34, a pair of posts 106A and 106B project from back face 68 of faceplate 36 at the opposing ends thereof. A threaded bore 108 passes vertically down through the side of each post 106. As shown in FIG. 3, holes 110A and 110B are formed on front face 42 of body 34 at the opposing ends thereof and are sized complimentary to posts 106A and B so that posts 106A and B can be received therein. As depicted in FIG. 5, bores 112A and 112B vertically extend up through bottom surface 40 of body 34 so as to intersect with holes 110A and 110B, respectively.

As depicted in FIG. 4, a first nut 120A and a second nut 120B are designed to be captured and freely slide within slide channel 100. Each nut 120 has a front face 122 and an opposing back face 124 with a threaded boar 126 centrally extending therebetween. Each nut 120 also has a top flat 128 and an opposing bottom flat 130 with rounded side faces 132 and 134 extending therebetween. Nuts 120A and B are configured so that they can freely and independently laterally slide within slide channel 100 but are prevented from rotating within slide channel 100. For example, nuts 120 are received within slide channel 100 so that top flats 128 are disposed adjacent to top wall portions 60A/98A while bottom flats 130 are disposed adjacent to bottom wall portions 60B/98B, as shown in FIG. 6. Nuts 120, however, are sized so that they can freely slide within slide channel 100 but are precluding from freely rotating within channel 100. That is, if a rotational force is applied to nuts 120 while in sliding channel 100, flats 128 and 130 strike against wall portions 60 and 98 so as to prevent nuts 120 from freely rotating within slide channel 100. Depending on their size and configuration, nuts 120 may be able to rotate within slide channel 100 over an angle, such as in a range between 5° and 90°, but they are typically precluded from rotating over an angle greater than 90°, 180° 270° or 360°.

As depicted in FIG. 2, fusion implant 10 also includes first locking screw 16A and second locking screw 16B. Although not required, locking screws 16A and 16B are typically identical. Each locking screw 16 includes a threaded shaft 144 having a first end 145 and an opposing second end 146. An enlarged head 148 secured to second end 146 of shaft 144. As depicted in FIGS. 2 and 4, enlarged head 148 has an encircling perimeter wall 150 having a cylindrical configuration and terminates at a terminal end face 152. An annular first chamfer 154 extends between second end 146 of shaft 144 and perimeter wall 150 while an annular second chamfer 156 extends between terminal end face 152 and perimeter wall 150. Chamfers 154 and 156 can be straight or rounded. For example, annular chamfers 154 and 156 can be conical, have an annular convex contour or have other tapered surfaces. Formed on terminal end face 152 is a driver recess 158. Driver recess 158 is typically in the form of a polygonal socket although other non-circular recesses that can receive a driver for engaging and rotation locking screw 16 can also be used.

During assembly, threaded shafts 144 of locking screws 16A and B are advanced through locking slots 88A and 88B, respectively, and are threaded into boars 126 of nuts 120A and 120B, respectively. Shafts 144 are advanced into nuts 120 until nuts 120 are received in their proper orientation within channel 92 on faceplate 36 (FIG. 4). In one embodiment, first end 145 of shaft 144 of each locking screw 16 is modified to help prevent locking screw 16 from unscrewing off of nuts 120. By way of example, the threads on the first end 145 of each shaft 144 can be deformed such as by compression, grinding, filing, melting or the like so as to prevent or at least make it more difficult to unscrew shafts 144 from nuts 120. In other embodiments, first end 145 of shafts 144 can be modified by securing a structure 149 to first ends 145 such as tape, adhesive, weld, flange, or the like that prevents or at least makes it more difficult to unscrew shafts 144 from nuts 120.

Next, posts 106A and 106B of faceplate 36 are received within holes 110A and 110B on body 34. Faceplate 36 and body 34 are pushed together so that back face 68 of faceplate 36 fits flushed against front face 42 of body 34. In this assembly, channels 54 and 92 are aligned together forming slide channel 100 in which nuts 120A and B are slidably received, as depicted in FIG. 6 and previously discussed. In an alternative embodiment, one of channels 54 or 92 could be eliminated while the other channel is made deeper so as to completely receive nuts 120A and 120B. Once faceplate 36 and body 34 coupled together, screws 138A and B (FIG. 5) are passed up through boars 112A and 112B, respectively, and are threaded into boars 108A and 108B extending through posts 106A and 106B of faceplate 36, thereby securing faceplate 36 to body 34. It is appreciated that other methods can also be used to secure faceplate 36 to body 34. For example, screws could be advanced through holes in faceplate 36 and threaded directly into body 34, thereby securing faceplate 36 to body 34. In this alternative embodiment, posts 106 and holes 110 could be retained or eliminated.

Figure 7A:
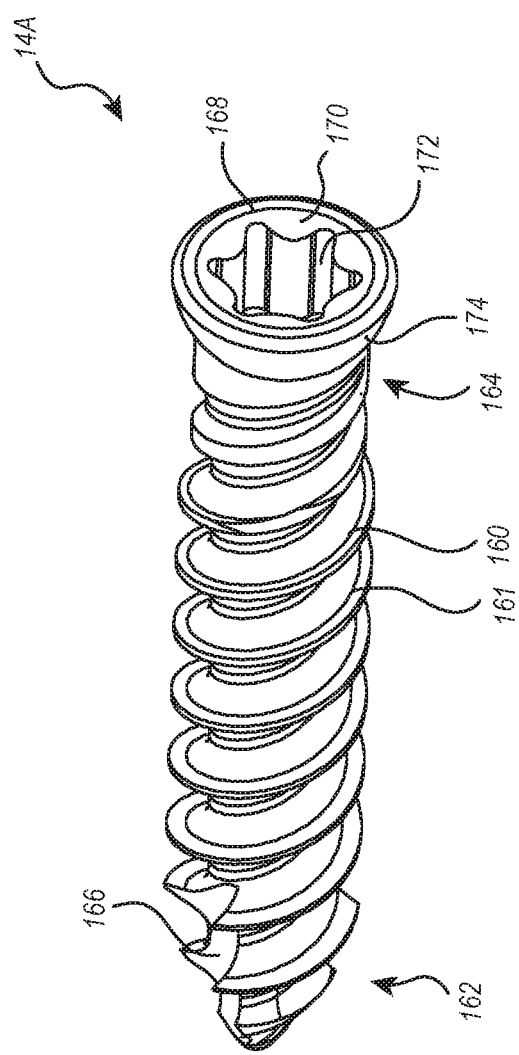
FIG. 7A is a front perspective view of the bone screw of the fusion implant shown in FIG. 1.
Figure 7B:
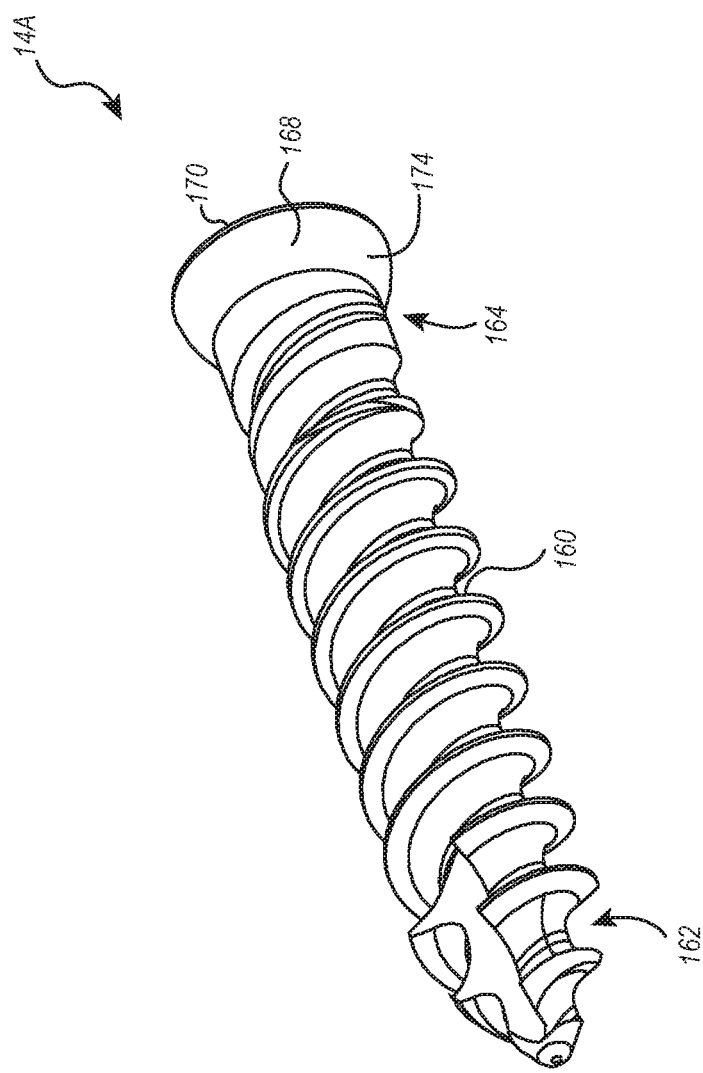
FIG. 7B is a rear perspective view of the bone screw shown in FIG. 7A.

Turning to FIGS. 7A and 7B, each bone screw 14 includes a shaft 160 having a helical thread 161 extending between a first end 162 and an opposing second end 164. First end 162 is tapered and can have one or more cutting slots 166 formed through threads 161 at first end 162. An enlarged head 168 is formed at second end 164 of shaft 160. Head 168 terminates at a terminal end face 170 having a driver recess 172 formed therein. Although driver recess 172 typically comprise a polygonal socket, driver recess 172 can comprise any size or shape of recess that functions to receive a driver for engaging and rotating bone screw 14. Head 168 has an annular tapered surface 174 that outwardly flares from second end 164 of shaft 160 to terminal end face 170. As previously discussed, bone screws 14 are sized and configured to pass through screw holes 80 for threading into bone, such as adjacent vertebrae, to thereby securely fix fusion implant 10 between adjacent vertebrae. As bone screws 14 are passed through screw holes 80, tapered surface 174 of bone screws 14 seats against annular chamfers 82 of faceplate 36 (FIG. 3) so as to prevent bone screws 14 from passing through faceplate 36.

Figure 8:
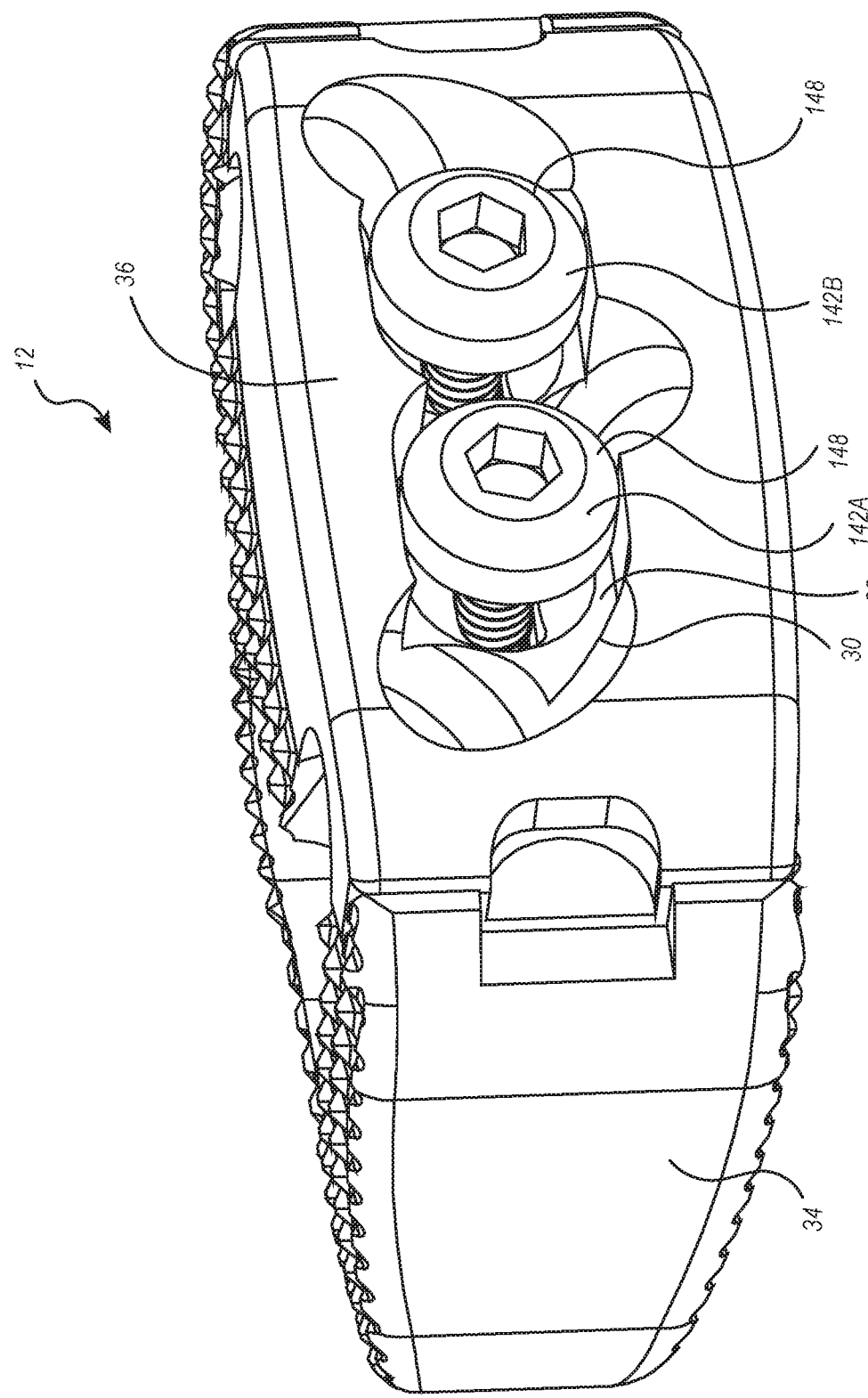
FIG. 8 is a perspective view of the fusion spacer shown in FIG. 3 in an assembled state with locking screws in a retracted first position.

As previously mentioned, with fusion implant 10 fully assembled, locking screws 16 are used to prevent bone screws 14 from unintentionally moving or backing out of fusion spacer 12. That is, by screwing locking screws 14 into and out of nuts 120, locking screws 14 can be moved between a retracted or first position and an advanced or second position. In the first position, as depicted in FIG. 8, locking screws 16 are only partially treaded into nuts 120 (FIG. 2) so that heads 148 of locking screws 16 are spaced back from interior surface 32 of recess 30. In this first position, locking screws 16 do not directly engaging faceplate 36. Rather, locking screws 16 are only loosely coupled to fusion spacer 12 so that locking screws can freely slide laterally within recess 30. More specifically, when locking screws 16 are in the first position, nuts 120 can freely slide laterally within slide channel 100 while locking screws 16 can concurrently freely slide laterally within locking slots 88 and recess 30 (FIG. 3). To enable locking screws 16 to laterally slide within locking slots 88, locking slots 88 typically have a longitudinal width that is at least 1.5, 2, 2.5, 3, 3.5 or 4 times the outer diameter of threaded shaft 144 of locking screws 16 or is in a range between any two of the foregoing. Furthermore, first end 145 of shafts 144 can project into access slots 66 (FIG. 6). As such, to enable shafts 144 to laterally slide within access slots 66, access slots 66 also typically have a longitudinal width that is at least 1.5, 2, 2.5, 3, 3.5 or 4 times the outer diameter of threaded shaft 144 of locking screws 16 or is in a range between any two of the foregoing.

With locking screws 16 in this first position, bone screws 14A-C can be advanced into corresponding screw holes 80A-C. As a bone screw 14 is advanced into a screw hole 80, the loosely positioned locking screw 16 can be easily pushed laterally out of the way to allow the bone screw 14 to be fully inserted within the corresponding screw hole 80. Locking screw 16 can be manually pushed to one side or, more commonly, as locking screw 16 is advanced, tapered surface 174 of bone screw 16 (FIG. 7B) rides against chamfer 156 on the outside of head 148 of locking screw 16 (FIG. 2) to automatically displace locking screw 16 and thereby permit passage of the bone screws 12 into the corresponding screw holes 80. The complementary angled slopes of tapered surface 174 and chamfer 156 assist in this automatic lateral displacement of locking screw 16.

Figure 9:
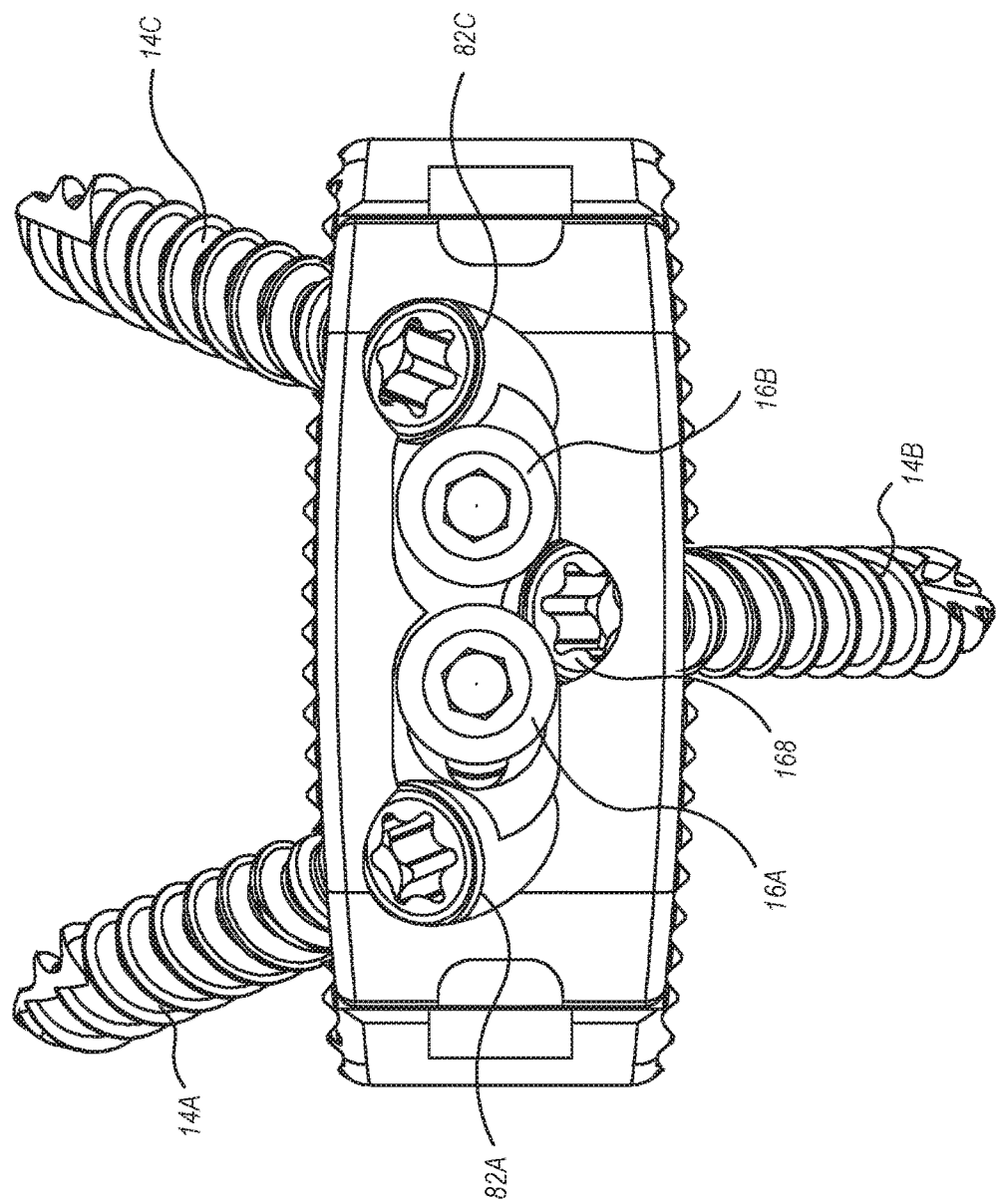
FIG. 9 is a front elevational view of the fusion implant shown in FIG. 1 with one of the locking screws in an laterally displaced position.
Figure 10:
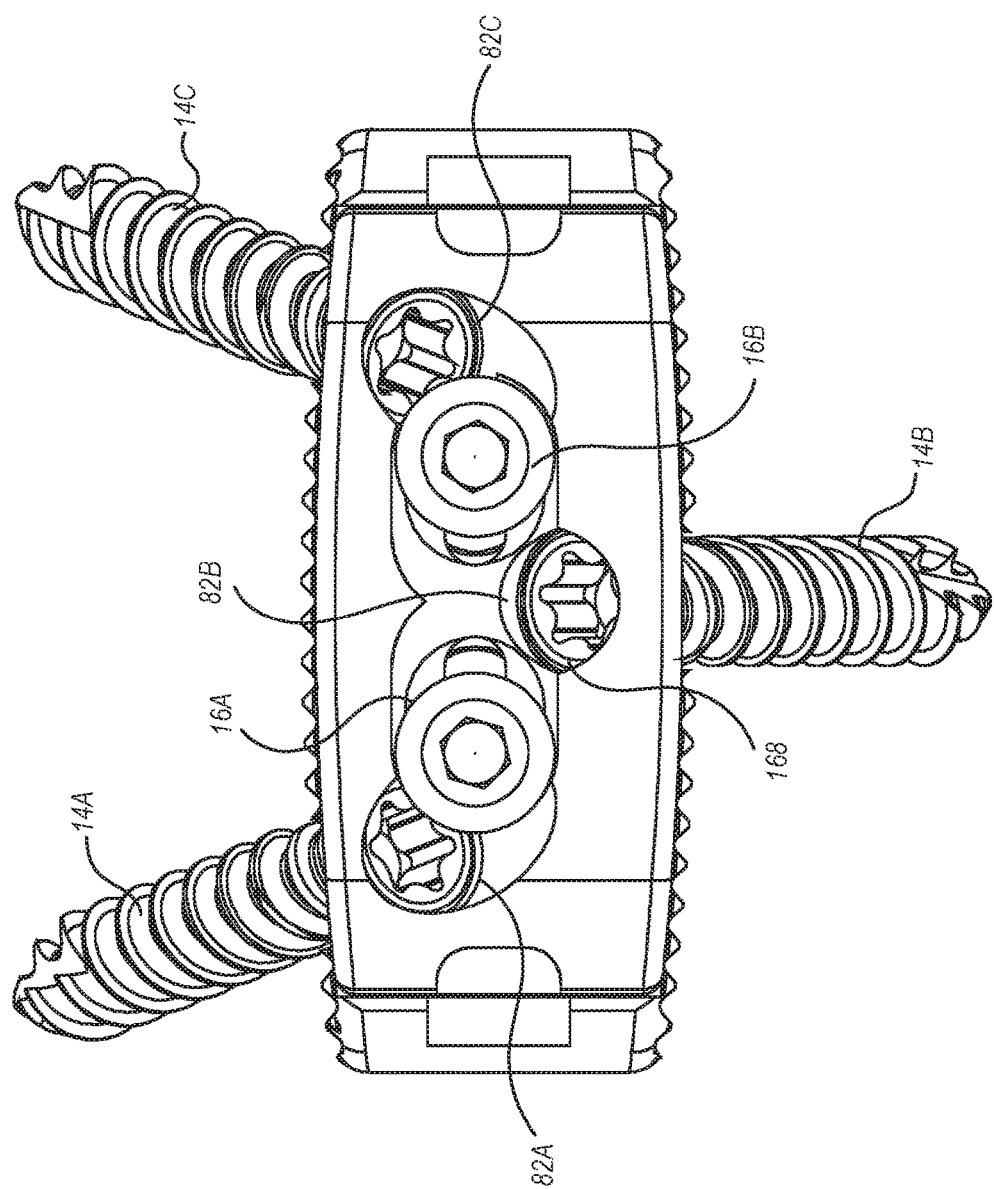
FIG. 10 is a front elevational view of the fusion implant shown in FIG. 1 with both of the locking screws outwardly laterally displaced.

By way of example, as shown in FIG. 9, locking screw 16A is displaced laterally or medially toward locking screw 16B and away from screw hole 82A so that bone screw 14A can freely advance into screw hole 82A. This displacement can be done manually or automatically as bone screw 14A is advanced into screw hole 82A. Likewise, locking screw 16B can be displaced laterally or medially toward locking screw 16A and away from screw hole 82C to enable bone screw 14C to freely advance into screw hole 82C. As depicted in FIG. 10, bone screw 14B can be advanced into screw hole 82B by laterally displacing locking screw 16A away from screw hole 82B and toward screw hole 82A and concurrently displacing locking screw 16B away from screw hole 82B and toward screw hole 82C. Again, locking screws 16A and B can be manually displaced but are more commonly automatically displaced by tapered surface 174 of head 168 of bone screws 14 pushing against chamfer 156 on the outside of head 148 of each of locking screw 16A and 16B.

Once bone screws 14 are properly positioned within screw holes 82, locking screws 16 can be moved to the advanced or second position. More specifically, a driver engages driver recess 158 and is used to rotate locking screws 16. As locking screws 16 are rotated, they are threaded into nuts 120 (which are prevented from rotating by flats 128 and 130) which in turn causes head 140 of locking screws 16 to advance into centering recesses 86 (FIG. 2). Because of complementary tapers between first chamfer 154 on head 148 of locking screws 16 (FIG. 4) and centering recess 86 (FIG. 3), locking screws 16 are automatically centered within centering recesses 86 as locking screws 16 are advanced into centering recess 86. That is, although locking screw 16A may be laterally displaced by the insertion of bone screw 14A as shown in FIG. 9 or by the insertion of bone screw 14B as shown in FIG. 10, as locking screw 16A is advanced into the second position, locking screw 16A is automatically centered within centering recess 86 as shown in FIG. 11.

Locking screws 16 are advanced until heads 140 are snugly seated against interior surface 32 of recess 30, as depicted in FIGS. 6 and 11. With locking screws 16 in this second position, locking screws 16 are fixedly secured to faceplate 36 of fusion spacer 12. Furthermore, locking screws 16 are positioned to prevent any unwanted movement or removal of bone screws 14 from fusion spacer 12. More specifically, locking screws 16 are position to obstruct the removal of bone screws 14. That is, if bone screws 14 try to back out of screw holes 80, bone screws 14 run into heads 148 of locking screws 16 which prevents bone screws 14 from backing out of fusion spacer 12 and thus also prevents any significant movement of bone screws 14. In one embodiment, heads 148 of locking screws 16 can extend over a portion of screw holes 80 to obstruct the removal of bone screws 14. However, because bone screws 14 are inclined at an angle toward corresponding locking screws, it is not necessary that heads 148 of locking screws 16 extend over a portion of screw holes 80 to obstruct the removal of bone screws 14. Rather, heads 148 can be disposed at the perimeter edge of screw holes 80 or slightly spaced back from the perimeter edge of screw holes 80 and still obstruct the removal of bone screws 14.

If it was subsequently desired to remove bone screws 14 from fusion spacer 12, locking screws 16 can again be moved back to their retracted or first position. Bone screws 14 could then be removed from screw holes 80 by laterally displacing locking screws 16.

Different embodiments of the present invention provided a number of unique advantages. For example, the present invention provides an easy mechanism for locking the bone screws to the fusion spacer so that the bone screws do not unintentionally back out of the fusion spacer or move beyond a tolerated amount. The inventive spinal implant is effective and easy to use. In addition, the present invention provides an easy mechanism for laterally displacing the locking screws to permit desired insertion and removal of the bone screws when desired. Furthermore, the present invention provides an easy mechanism for the self-centering of the locking screws as they are moved to their advanced or second position. The present invention also restricts full removal of the locking screws from the fusion spacer to help ensure that the locking screws can be easily moved between the first and second positions without risk the locking screws being detached or lost. Different embodiments of the present invention also have other benefits.

The present invention may be embodied in other specific forms without departing from its spirit or essential characteristics. For example, the placement, orientation and number of bone screws and locking screws can be modified as needed. For example, in one embodiment, only two bone screws may be used and thus only one locking screw may be required.

The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An interbody spinal fusion implant comprising:
   a fusion spacer having a top surface and an opposing bottom surface that extend between a front face and an opposing back face, a recess being formed on the front face and being at least partially bounded by an interior surface, a first screw hole passing through the interior surface of the recess;
   a first nut disposed between the front face and the opposing back face of the fusion spacer;
   a first bone screw being received within the first screw hole; and
   a first locking screw at least partially disposed within the recess of the fusion spacer and threaded into the first nut, the first locking screw being movable between an advanced position and a retracted position, when the first locking screw is in the retracted position, the first locking screw is secured to the fusion spacer by threaded engagement with the first nut but can freely slide laterally within the recess to enable the first bone screw to be freely removed from the first screw hole, when the first locking screw is moved to the advanced position, the first locking screw is held fixed relative to the fusion spacer and obstructs removal of the first locking screw from the first screw hole.

2. The interbody spinal fusion implant as recited in claim 1, wherein the first locking screw partially covers the first screw hole.

3. The interbody spinal fusion implant as recited in claim 1, further comprising:
   a second screw hole passing through the interior surface of the recess at a location spaced apart from the first screw hole; and
   a second bone screw being received within the second screw hole, wherein when the first locking screw is in the retracted position, the first locking screw can freely slide laterally within the recess to enable the second bone screw to be freely removed from the second screw hole, and when the first locking screw is moved to the advanced position, the first locking screw partially covers the second screw hole so as to block removal of the second locking screw from the second screw hole.

4. The interbody spinal fusion implant as recited in claim 1, wherein the fusion spacer comprises:
   a body having a top surface and an opposing bottom surface that extend between a front face and an opposing back face; and
   a faceplate having a top surface and an opposing bottom surface that extend between a front face and an opposing back face, the back face of the faceplate being secured to the front face of the body, wherein the recess is formed on the front face of the faceplate and a first locking slot having an elongated width extends through the faceplate from the interior surface of the recess.

5. The interbody spinal fusion implant as recited in claim 4, further comprising:
   the first locking screw having a head and a threaded shaft extending from the head, the threaded shaft passing through the first locking slot; and
   the first nut disposed between the body and the faceplate, the shaft of the first locking screw being threadedly engaged with the first nut.

6. The interbody spinal fusion implant as recited in claim 5, wherein a length of the elongated width of the first locking slot is at least 2 times the diameter of the threaded shaft of the first locking screw.

7. The interbody spinal fusion implant as recited in claim 5, wherein the head of the first locking screw comprises:
   a terminal end face on which a driver recess is formed;
   an encircling side surface; and
   an annular chamfer that extends from the side surface to the terminal end face.

8. The interbody spinal fusion implant as recited in claim 5, further comprising an elongated channel laterally recessed along the back face of the faceplate or along the front face of the body, the first nut being received within the channel so that the first nut can laterally slide within the channel but is precluded from rotating within the channel.

9. The interbody spinal fusion implant as recited in claim 4, further comprising:
   the head of the first locking screw having a bottom surface from which the threaded shaft extends and an opposing top surface, the bottom surface comprising an annular tapered surface; and
   a centering recess being formed on interior surface of the recess of the fusion spacer, the first locking slot extending through the centering recess.

10. The interbody spinal fusion implant as recited in claim 9, wherein the centering recess has a taper that is complementary to the annular tapered surface of the first locking screw.

11. An interbody spinal fusion implant comprising:
   a body having a top surface and an opposing bottom surface that extend between a front face and an opposing back face;
   a faceplate secured to the front face of the body, the faceplate having a top surface and an opposing bottom surface that extend between a front face and an opposing back face, a recess being formed on the front face of the faceplate and being at least partially bounded by an interior surface, a first screw hole and a spaced apart first locking slot passing through the faceplate from interior surface of the recess, the first locking slot having an elongated width;
   a first locking screw having a head and a threaded shaft extending from the head, the threaded shaft passing through first locking slot and being sized so that the threaded shaft can slide laterally along a length of the elongated width of the first locking screw; and
   a first nut disposed between the body and the faceplate, the shaft of the first locking screw being threadedly engaged with the first nut.

12. The interbody spinal fusion implant as recited in claim 11, wherein the first locking screw is movable between a retracted position wherein the first locking screw can freely slide laterally within the first locking slot and an advanced position wherein the first locking screw is held fixed relative to the faceplate and partially covers the first screw hole.

13. The interbody spinal fusion implant as recited in claim 12, further comprising:
   a second screw hole passing through the faceplate from interior surface of the recess; and
   a second bone screw received within the second screw hole, the second bone screw being blocked from removal by the first locking screw when the first locking screw is in the advanced position.

14. The interbody spinal fusion implant as recited in claim 11, further comprising a first bone screw received within the first screw hole, the first bone screw being blocked from removal by the first locking screw.

15. The interbody spinal fusion implant as recited in claim 11, wherein the length of the elongated width of the first locking slot is at least times the diameter of the threaded shaft of the first locking screw.

16. The interbody spinal fusion implant as recited in claim 11, further comprising:
   the head of the first locking screw having an annular tapered surface that encircles the shaft; and
   a centering recess being formed on interior surface of the recess of the fusion spacer, the first locking slot extending through the centering recess.

17. The interbody spinal fusion implant as recited in claim 11, further comprising an elongated channel laterally recessed along the back face of the faceplate or along the front face of the body, the first nut being received within the channel so that the first nut can laterally slide within the channel but is precluded from rotating within the channel.

18. A method for locking a bone screw of an interbody spinal fusion implant, the method comprising:
   advancing a first bone screw into a first bone screw hole of a fusion spacer so that the first bone screw laterally displaces in a first direction a first locking screw that is loosely secured to the fusion spacer in a retracted position; and screwing the first locking screw into an advanced position on the fusion spacer so that the first locking screw is held fixed relative to the fusion spacer and the first locking screw blocks removal of the first bone screw from the fusion spacer.

19. The method as recited in claim 18, wherein the first locking screw self-aligns into a centered position as the first locking screw is screwed into the fusion spacer.

20. The method as recited in claim 18, further comprising prior to the step of screwing the first locking screw:
   advancing a second bone screw into a second bone screw hole of the fusion spacer so that the second bone screw laterally displaces in a second direction the first locking screw that is loosely secured to the fusion spacer in the retracted position; and
   wherein the step of screwing the first locking screw into the advanced position causes the first locking screw to block removal of the first bone screw and the second bone screw from the fusion spacer.

21. The method as recited in claim 20, wherein the second direction of the first locking screw is opposite the first direction of the first locking screw.

22. The method as recited in claim 18, further comprising:
   unscrewing the first locking screw from the advanced position to the retracted position; and
   removing the first bone screw from first bone screw hole of the fusion spacer so that the first bone screw laterally displaces in the first direction the first locking screw.

23. An interbody spinal fusion implant comprising:
   a fusion spacer having a top surface and an opposing bottom surface that extend between a front face and an opposing back face, a recess being formed on the front face and being at least partially bounded by an interior surface, a first screw hole passing through the interior surface of the recess and being configured to receive a bone screw, the fusion spacer further comprising:
      a body having a top surface and an opposing bottom surface that extend between a front face and an opposing back face; and
      a faceplate having a top surface and an opposing bottom surface that extend between a front face and an opposing back face, the back face of the faceplate being secured to the front face of the body, wherein the recess is formed on the front face of the faceplate and a first locking slot having an elongated width extends through the faceplate from the interior surface of the recess; and
   a first locking screw at least partially disposed within the recess of the fusion spacer, the first locking screw being movable between an advanced position and a retracted position, when the first locking screw is in the retracted position, the first locking screw is secured to the fusion spacer but can freely slide laterally within the recess, when the first locking screw is moved to the advanced position, the first locking screw is held fixed relative to the fusion spacer.

* * * * *